United States Patent [19]
Allen et al.

[11] Patent Number: 5,589,168
[45] Date of Patent: Dec. 31, 1996

[54] PROBIOTIC

[75] Inventors: William D. Allen; Margaret A. Linggood; Philip Porter, all of Bedford, Great Britain

[73] Assignee: Unilever Patent Holdings B.V., Vlaardingen, Netherlands

[21] Appl. No.: 300,207

[22] Filed: Sep. 2, 1994

Related U.S. Application Data

[63] Continuation of Ser. No. 864,992, Apr. 8, 1992, abandoned.

[30] Foreign Application Priority Data

Apr. 8, 1991 [GB] United Kingdom ............... 9107305

[51] Int. Cl.$^6$ ............................. C12R 1/46; A61K 35/74; A23C 9/12
[52] U.S. Cl. ................ 424/93.4; 424/93.44; 424/439; 426/71
[58] Field of Search .................... 424/439, 93.44, 424/93.48, 93.4; 426/61, 71

[56] References Cited

U.S. PATENT DOCUMENTS

| | | | |
|---|---|---|---|
| 4,579,733 | 4/1986 | Kawai et al. | 424/93 H |
| 4,710,379 | 12/1987 | Kawai et al. | 424/93.44 |
| 4,797,278 | 1/1989 | Kawai et al. | 424/93 H |
| 5,116,737 | 5/1992 | McCoy | 435/42 |
| 5,292,657 | 3/1994 | Rutherford et al. | 435/243 |
| 5,340,577 | 8/1994 | Nisbet et al. | 424/93.21 |
| 5,478,557 | 12/1995 | Nisbet et al. | 424/93.21 |
| 5,501,857 | 3/1996 | Zimmer | 424/438 |

FOREIGN PATENT DOCUMENTS

| | | |
|---|---|---|
| 3509239 | 9/1986 | Germany. |
| 1083025-A | 3/1989 | Japan. |

OTHER PUBLICATIONS

Wadstrom, "Streptococcus . . . Rabbit Model" Zentralblatt Bakteriol Mikrobiol Hyg Ser A, 257(3) pp. 357–363 (1984).
Gade et al., "Paraghurt for Patients with IBS" Scandanavian Journal of Primary Health Care, 7(1) pp. 23–26 (1989).
Biological Abstracts, vol. 79, No. 2, Philadelphia, PA, US, Abstract No. 14131, (1985).
Gade et al., "Paraghurt for Patients with Irritable Bowel Syndrome, A controlled Clinical investigation from General practice", Scandinavian Journal of Primary Health Care, vol. 7, No. 1, pp. 23–26, (Mar. 1989).
Scandanavian Journal of Primary Health Care, vol. 7, No. 1, 1989, Stockholm, pp. 23–26.
Manning et al., Towards positive diagnosis of the irritable bowel, Medical Journal, 1978, 2, pp. 653–654.
Drossman et al, Bowel Patterns Among Subjects Not Seeking Health Care, Gastroenterology 1982; 83, pp. 529–534.
Burke et al, Adhesive Eschericha coli in inflammatory bowel disease and infective diarrhoea, BMJ, vol. 297, Jul. 1988.
Rask–Madsen et al, The Irritable Bowel Syndrome: The Role of Intestinal Secretion, Grune & Stratton, 1985.
Harvey et al, A Simple Index of Crohn's–Disease Activity, The Lancet, Mar., p. 514.
Watson, MD, PhD, et al, Globus and headache: common symptoms of the irritable bowel syndrome, CMA Journal, vol. 118, Feb. 1978, pp. 386–389.
Jones et al, Food Intolerance: A Major Factor In The Pathogenesis of Irritable Bowel Syndrome, The Lancet, Nov. 1982, pp. 1115–1117.
Tilbe, MD et al, The extracolonic manifestations of the irritable bowel syndrome, Canadian Medical Association, Journal, 1990, 142(6), pp. 539–540.
Hunter et al, Studies on the Pathogenesis of Irritable Bowel Syndrome Produced By Food Intolerance, Grune & Stratton, 1985, pp. 185–191.
Krag, Irritable bowel syndrome: current concepts and future trends, Dept. of Gastroenterology, Denmark, pp. 107–115.

*Primary Examiner*—John C. Bleutge
*Assistant Examiner*—Robert H. Harrison
*Attorney, Agent, or Firm*—Cushman Darby & Cushman, LLP

[57] ABSTRACT

A novel strain of *Enterococcus faecium*, deposited as NCIMB 40371, has valuable probiotic properties and is particularly effective in alleviating symptoms of irritable bowel syndrome in human patients. The novel strain can be used in the manufacture of human foodstuffs.

4 Claims, No Drawings

PROBIOTIC

This is a continuation of application Ser. No. 07/864,992, filed on Apr. 8, 1992, which was abandoned upon the filing hereof.

This invention relates to so-called "probiotic" organisms, and to compositions containing them, which are useful for promoting or maintaining the health and general well-being of humans and animals.

By the invention we have discovered a novel strain of *Enterococcus faecium* bacterium (hereinafter referred to as strain PR88) which shows particular favourable abilities in colonising the human gastrointestinal system, and in alleviating symptoms of gastrointestinal disorders especially so-called "irritable bowel syndrome" (IBS). Strain PR88 confers similar benefits in cases of other severe abdominal complaints, such as so-called "inflammatory bowel disease" (IBD). The beneficial properties of strain PR88 may also facilitate the re-establishment of normal gastroenteric functions in human patients who have undergone severe abdominal surgery or other treatments (such as chemotherapy or radiotherapy) which have resulted in their natural gastroenteric functions becoming unbalanced.

Administration of the strain to individuals who, although exhibiting no disease symptoms, may nevertheless be susceptible to gastroenteric disorders, can help to maintain or indeed enhance their state of health. An example of such occasional disorder is "traveller's diarrhoea", which may be induced by the stress of travelling or infection by a pathogenic micro-organism not previously encountered by the traveller.

Further, the strain PR88 can advantageously be administered to animals, especially domesticated mammals such as pigs, cattle, horses and domestic pets.

A sample of strain PR88 has been deposited on 25 February 1991 in accordance with the provisions of the Budapest Treaty, in the National Collections of Industrial and Marine Bacteria Limited, Aberdeen, under Accession No. NCIMB 40371.

More generally, the invention provides Entercococcus organisms which, if administered as a single oral dose of $10^{11}$ viable organisms to a human patient diagnosed as suffering from IBS, maintain a faecal excretion rate of at least $10^5$ Enterococcus organisms per gm of wet faeces from said patient for more than 5 days post-treatment, and alleviate one or more symptoms of IBS in said patient within 28 days, preferably 14 days, post-treatment. Preferred organisms of the invention are capable of alleviating one or more symptoms of IBS within 10 days, more preferably within 7 days, post-treatment. Preferred organisms can also maintain the desired faecal excretion rate for more than 10 days post-treatment.

In a further general embodiment, the invention provides Enterococcus organisms which, if administered as single daily oral doses each of $10^{10}$ viable organisms, over a continuous period of 14 days, (preferably merely 10 days) to a human patient diagnosed as suffering from IBS, maintain a faecal excretion rate of at least $10^5$ Entercococcus organisms per gm of wet faeces from said patient throughout said treatment period and alleviate one or more symptoms of IBS in said patient during said treatment period.

For convenience, the expression "strain PR88" will be used hereinafter to include any Entercococcus strain encompassed by the general definitions given in the two immediately preceding paragraphs.

One embodiment of the invention resides in the novel strain PR88 itself. The invention extends to mutants and derivatives of strain PR88 which exhibit similar or greater probiotic efficacy, especially in relation to IBS.

A further embodiment is the use of strain PR88 in the treatment of humans or animals.

The invention provides an edible composition for administration to a human patient exhibiting symptoms of gastroenteric disorder, comprising viable organisms of strain PR88 in a carrier material. Preferably, the carrier material is aqueous. The carrier material should be pharmaceutically-acceptable.

The composition will normally be packaged with instructions recommending a mode of administration to the patient, e.g. specifying dosage quantity and frequency of administration, based on clinical trials conducted with a particular formulation in accordance with the invention.

A further embodiment of the invention is the use of strain PR88 in the manufacture of a composition for administration to humans or animals. Such a composition can comprise, for example, organisms of strain PR88 in a pharmaceutically acceptable carrier medium which can be fed to a patient or administered by intubation. Alternatively, lyophilised viable PR88 organisms can be dispensed in solid form, e.g. as a capsule.

The invention also comprises edible products such as fermented milk products, e.g. yoghurts, containing strain PR88. Non-milk based products can also be provided, such as yoghurt-like compositions containing milk substitutes such as soya. The strain can also be incorporated in the aqueous phase of edible emulsions, such as margarine, low-fat spreads, or dressings.

Typically, the composition will contain at least about $10^3$, preferably at least about $10^6$, and ideally from about $10^9$ to about $10^{10}$ viable PR88 organisms per gm.

The strain PR88 can be cultured industrially to provide commercial quantities of organisms, by growth under typical bacterial fermentation conditions.

The strain can be supplied commercially as a concentrate in an edible carrier (e.g. water) which does not induce growth of the bacteria. Another alternative is a freeze dried composition containing viable PR88 organisms. Such compositions can be added to appropriate foodstuffs during manufacture of the foodstuffs, to provide probiotic products. Care should be taken that subsequent processing of the foodstuff does not lead to the loss of the desired probiotic activity.

Edible Capsules, made for example from gelatin, containing the strain PR88 (preferably in lyophylised form) can be a useful product form for prophylactic or therapeutic use.

Although PR88 is capable of fermenting milk, it is not especially efficient in this respect. If PR88 is to be incorporated in a probiotic yoghurt, for example, it may be convenient to produce the yoghurt by means of a conventional yoghurt strain, e.g. a Lactobacillus, and to add the PR88 organisms later.

The invention also extends to the use of strain PR88 as a probiotic additive in human foods or animal feed.

Although it is envisaged that strain PR88 will generally be used in the form of intact viable cells, the invention also extends to non-viable cells of strain PR88 such as killed cultures and other compositions containing beneficial factors expressed by strain PR88.

Important embodiments of the invention are:
1. An edible composition comprising viable organisms of strain NCIMB 40371, packaged with instructions recommending a mode of administration to a human patient exhibiting symptoms of gastroenteric disorder;
2. a controlled diet for a human patient exhibiting symptoms of IBS, including such a composition;

3. a method of alleviating symptoms of gastroenteric disorder, specially IBS in a human patient by the oral administration of an edible composition comprising viable organisms of strain NCIMB 40371, the composition being administered in an amount sufficient to establish and/or maintain a population of said strain in the gastroenteric tract of said human patient; and 4. a method of alleviating symptoms of IBS in a human patient by the repeated administration of a fermented milk product containing viable organisms of strain NCIMB 40371.

Irritable Bowel Syndrome (IBS)

Although individuals later diagnosed as suffering from IBS form a very large proportion of the patients seen by gastroenterologists (20–50%) there are no simple tests to confirm the diagnosis. However the symptoms most frequently associated with the condition are:

1. Abdominal pain relieved by bowel movement
2. Loose stools associated with the pain
3. More frequent stools associated with the pain
4. Abdominal distension
5. Mucus in the stool
6. A sense of incomplete evacuation (Manning et al, 1978)

If no other organic disorder can be found to account for the above symptoms the diagnosis is usually IBS.

As well as the recognised colonic symptoms listed above there may be additional extracolonic symptoms associated with the disease, these include chronic headache or migraine and swelling and pain in the joints (Tilbe & Sullivan, 1990; Watson et al, 1978).

The individuals seen and diagnosed as IBS cases by clinicians may only represent 'the tip of the iceberg'. Epidemiological surveys in the UK, the USA and Denmark showed that 14%, 17% and 15% respectively of apparently healthy individuals had experienced more than 6 episodes of lower abdominal pain with at least 3 of the typical six IBS symptoms during the previous year: Drossman et al (1982), Krag (1985), Thompson and Heaton (1980). So only a minority of individuals with IBS (presumably the more severe cases plus individuals prone to seek medical advice on all possible occasions) go to their doctors with the problem. The majority of the sufferers either put up with it or try assorted home remedies, most of which are unproven and probably useless.

Causes of IBS Symptoms

Individuals suffering from IBS experience disturbances in the motility of both the upper and lower gut, and these can lead to diarrhoea and/or constipation and pain. The abnormal gut function could be due to a disturbance of intestinal control. The extracolonic manifestations of the syndrome, such as chronic headache and migraine, imply that an agent acting systemically could also be involved (Watson et al 1978).

It has been suggested that prostagladin E2 (PGE) may act as a intestinal mediator in the diarrhoeal form of IBS. Exogenous PGE exerts a potent secretory effect on the intestinal epithelium and can evoke copious watery diarrhoea in humans following oral, intrajejunal or parenteral administration. PGs also affect intestinal motility. PGE is synthesized locally in the small intestine and its synthesis/release is normally under hormonal and neutral control. Abnormal release of PGE would clearly give rise to adverse symptoms and individuals with IBS-diarrhoea often do have higher than normal PGE levels (Rask-Madsen & Bukhave, 1985). One condition that may trigger the release of PGE is food intolerance. Jones et al (1982) reported that specific foods provoked symptoms of IBS in 14/21 patients and this was associated with increased levels of rectal PGE.

Many patients can date the onset of their IBS to a definite event such as a bout of gastroenteritis, abdominal or pelvic surgery, or a course of antibiotics. Women undergoing hysterectomy are far more likely to develop IBS symptoms post-operatively if they are given metronidazole following the operation. This indicates that if the gut flora is disturbed a new gut ecosystem may gain dominance that makes the patient more prone to IBS (Hunter and Jones, 1985). A chronic infection with a hitherto unidentified pathogen or enteroadherent E.coli has been suggested as the course of IBS and inflammatory bowel disease in a proportion of patients (Borody et al, 1989; Burke and Axon, 1988) but another possibility is that the stressed gut can be colonised by bacteria which are harmless generally but can metabolize certain foodstuffs to give intermediates which can trigger PGE release.

Probiotic therapy can benefit IBS patients, but it is necessary to identify a suitable bacterial strain. The mode of action of probiotics is not at present well-understood. The following three parameters seem important.

1. The strain should be a natural intestinal strain, non-pathogenic and non-toxic.
2. A suitable, safe delivery system should be available for giving the patient large numbers of viable cells.
3. The strain should be capable of surviving and metabolizing in the gut environment, e.g. be resistant to low pH and organic acids.

METHODS

Strain and Growth Media

Strain PR88 is a naturally-occurring gram-positive coccus identified as *Streptococcus (Enterococcus) faecium*. The API 20S code of the strain is 5357 511 (very good identification *Ent.faecium*) and it grows on thallous acetate—tetrazolium glucose agar giving white colonies.

PR88 will ferment sugars such as glucose to give acids thereby lowering the pH to about 4.5 and will "yoghurt" milk media after 19–24 hours at 37° C but the yoghurts used in this study were incubated for 48 hours (a milk-intolerant patient was found to react to 24h, but not 48h, yoghurts). Counts of PR88 in the yoghurts were usually between $10^8$ and $10^9$ per gram and the pH was about 4.6.

PR88 was grown in 500 ml aliquots of GYSM* for intracaecal inoculation and 100 ml aliquots of DS* for oral inoculation.

*GYSM—10gm glucose, 3 gm yeast extract (Oxoid L21) and 100 gm milk powder (Oxoid L31) per litre.

*DS—10 gm glucose and 100 gm milk powder (Oxoid L31) per litre.

Batches of set GYSM and 'yoghurts' (individual pots of set DS) were checked to confirm that they were pure cultures of PR88 by plating on blood agar and incubating plates at 37° C both aerobically and anaerobically.

Examination of Faecal Samples

Faecal samples from the patients were examined before the start of yoghurt therapy and then each week during the trial. The stool samples were first examined microscopically for abnormalities (ova, cysts, parasites, pus cells, red blood cells, mucus etc) and then 'counted' by the method of Miles and Misra (1938) to determine faecal levels of different types of bacteria. The different types of bacteria were enumerated by counting on different selective media and incubating the plates aerobically and anaerobically at 37° C.

This enabled us to determine the viable counts/gm faeces of *Ent.faecium, Ent.faecalis*, enterobacteria, anaerobes and yeasts. When necessary, preliminary identification was confirmed by microscopy and biochemical tests.

Subjects Tested

Seventeen patients with chronic IBS who had previously failed to respond to conventional treatment were selected, and their clinical condition monitored- Nine were 'high volume diarrhoea' (HVD) cases, the remaining eight had intermittent diarrhoea or other IBS symptoms (Table 1)The average daily faecal weights of the HVD patients were measured (over a period of 3–4 days) before and after treatment. The condition scores of all patients were assessed before and after treatment by the simple index method of Harvey and Bradshaw (1980). In twelve of the patients, the PR88 culture was initially administered by intracaecal intubation and their intestinal PR88 levels were then maintained by daily yoghurts. Five patients had the oral yoghurt therapy only (see Table 1). Later, each individual reduced their yoghurt consumption (one pot every second or third day) until they reached what they considered to be the right frequency to maintain improved health.

By the end of the trial, patients had been treated with PR88 for periods varying from 4 months to 2.5 years.

RESULTS

General Bacteriology

The faecal bacteriology of healthy individuals as measured by anaerobe/aerobe ratios can vary considerably from day to day although it is possible to calculate the 'normal range' for faecal samples treated in a standard way.

The faecal bacteriology counts of IBS patients gave a higher percentage of abnormal anaerobe/aerobe ratios than healthy individuals, but after probiotic treatment gave ratios in the normal range. However, the abnormal ratios could be either above or below the norm and many IBS patients gave similar ratios when normal and when in diarrhoeal breakdown. Therefore it can be inferred that although some IBS patients may have an abnormal faecal flora as measured by crude anaerobe/aerobe ratios but there is no characteristic IBS profile. (Imbalances within the aerobe or anaerobe group would not be shown up by this method).

None of the IBS patients had detectable levels of *Ent.faecium* in their stools before treatment. However many healthy individuals do not appear to carry. *Ent.faecium* either.

The effects of the yoghurt therapy in all 17 patients included in the trial are summarised in Table 2. The therapy was successful in 7/9 HVD patients and in 5/8 of the others. The two failures in the HVD (patients 8 and 9) group reacted adversely to the yoghurts; they were normally intolerant of dairy foods and were clearly affected by some factor in the milk that was not changed by the yoghurting process.

The average daily faecal weights of patients (1) to (7) before and after treatment are given in Table 3; whereas prior to treatment they were high, after treatment they returned to the normal range.

The assessment of the other IBS symptoms was necessarily more subjective than the measurement of faecal weights but it was possible to obtain a "symptoms index" (method of Harvey and Bradshaw, 1980) from each patient "before" and "after"—see Tables 4 and 5. Therapy with strain PR88 reduced the abdominal pain, migraine-like headaches and joint pains associated with IBS in the twelve successful patients and, with the exception of patient (2), these symptoms returned if PR88 therapy was terminated.

DISCUSSION

The public have a conception of yoghurt as a 'health-giving food' but scientific evidence of the beneficial properties of fermented milk products is rather tenuous. One reason for this is that the strains of bacteria used for the commercial production of yoghurt (*Lact.bulgaricus* and *Strep.thermophilus*) and other fermented milk products have been selected for rapid growth in vitro and their ability to produce foodstuffs of a pleasant taste. These strains have largely lost the ability to survive in vivo so a probiotic effect with ordinary commercial yoghurts is rather unlikely. However, the *Ent.faecium* PR88 has the ability to adhere to gut cells and survive in the intestinal environment. PR88 yoghurts milk much more slowly than a commercial culture but it can survive and proliferate in the alimentary tract. Early experiments in patients showed that after intubation, PR88 could implant and maintain large intestinal populations for several weeks. Later experiments showed that yoghurts taken orally could also result in high numbers of the strain in the intestine, as patients in the trial usually had faecal levels of PR88 of $10^6$–$10^9$ per gram.

Probiotic therapy with PR88 was very effective at alleviating the symptoms of IBS, particularly diarrhoea-associated IBS. The average daily faecal weights of the patients were determined before and after probiotic treatment and clearly demonstrated the efficacy of PR88. In 5/7 IBS patients with the diarrhoeal syndrome the average daily faecal weight was brought down to normal levels by probiotic therapy. The two 'failures' were both intolerant of cow's milk and also reacted adversely to dairy yoghurts. The three patients with intermittent diarrhoea also responded well to yoghurt treatment as did 2 individuals with IBS without diarrhoea. The other symptoms of IBS such as abdominal pain, migraine-like headache and arthritic pains and swelling of the joints could also be relieved by the probiotic therapy (see Table 4)

Many (but not all) of the IBS patients were initially given PR88 by intracaecal tube in an attempt to get a rapid improvement in their condition. Intracaecal intubation bypasses the stomach and enables PR88 to be delivered directly into the lower intestine. As it was found that most patients responded successfully to oral yoghurt therapy alone, intubation was discontinued.

We found yoghurts to be a safe and efficient means of administering PR88. Viable counts were about $10^8$/ml so one yoghurt contained $10^{10}$ bacteria. The yoghurt pH was about 4.5 so this reduced the risks of contamination; pathogens such as salmonella and listeria are not able to survive at low pHs. PR88 survived well in the acid yoghurt environment and the yoghurt-grown bacteria were in a suitable metabolic state to colonise the gut.

The patients suffering from IBS who were involved in this trial were severe, chronic cases with whom all conventional other types of therapy had failed. Most of them had suffered from IBS for 10–20 years and so were most unlikely to recover spontaneously during our test period. Similarly although IBS symptoms can be influenced by psychological factors previous types of therapy had not induced a 'psychological cure' in these patients. PR88 therapy was tested on long term, well understood IBS patients and the improvements in their condition and quality of life were genuine.

TABLE 1

Summary of IBS Patients treated with *Ent. Faecium* PR88

| | Length of | Date commenced probiotic therapy | |
|---|---|---|---|
| Patient | time with IBS (years) | i/c tube, then yoghurt, | oral yoghurt only |
| A. High volume diarrhoea cases | | | |
| 1. | 10 | 6/88* | — |
| 2. | 12 | 4/89 | — |
| 3. | 20 | 9/89 | — |
| 4. | Not Known | — | 12/89 |
| 5. | 7 | 3/90 | — |
| 6. | 10 | — | 6/90 |
| 7. | 10 | 3/90 | — |
| 8. | Not Known | 10/90 | — |
| 9. | Not Known | 6/90 | — |
| B. Others | | | |
| 10.** | 2 | — | 3/90 |
| 11.** | 5 | 2/90 | — |
| 12.** | 10 | 8/90 | — |
| 13. | Not Known | 2/90 | — |
| 14. | 20 | 7/90 | — |
| 15. | Not Known | — | 6/90 |
| 16. | Not Known | — | 6/90 |
| 17. | Not Known | 1/90 | — |

*initially intubation only
**intermittent diarrhoea.

TABLE 2

Summary of IBS Patients treated with *Ent. Faecium* PR88

| Patient | Reported improvement after yoghurt therapy | Viable count/gm faeces of PR88 after treatment |
|---|---|---|
| A. High volume diarrhoea cases | | |
| 1. | + | $10^5$–$10^9$ |
| 2. | + | $10^7$–ND (normalisation of gut flora) |
| 3. | + | $10^5$–$10^9$ |
| 4. | + | $10^5$–$10^8$ |
| 5. | + | $10^7$–$10^8$ |
| 6. | + | $10^6$–$10^8$ |
| 7. | + | $10^6$–$10^8$ |
| 8. | − lactose intolerant | $10^5$ |
| 9. | − lactose intolerant | $10^8$–$10^9$ |
| B. Others | | |
| 10.* | + | $10^6$–$10^8$ |
| 11.* | + | $10^7$–$10^8$ |
| 12.* | + | $10^8$–$10^9$ |
| 13. | + | $10^7$–$10^9$ |
| 14. | + | $10^8$ |
| 15. | − | $10^6$–$10^9$ |
| 16. | − | $10^7$–$10^9$ |
| 17. | − | $10^8$ |

*intermittent diarrhoea
None of the above had *Ent. faecium* before treatment

TABLE 3

The average daily faecal weights of the patients before and after probiotic treatment

| Patient/ dates | Average daily faecal weight | PR88/ g. faeces | Comments |
|---|---|---|---|
| Patient 1 | | | |
| 21–23/9/88 | 3080 | ND | Food intol. breakdown |
| 18/10/88 | 250 | $2 \times 10^6$ | After intubation. |
| 7–9/6/89 | 3643 | ND | Antibiotic breakdown |
| 19/6/89 | 200 | $8 \times 10^7$ | After intubation/yoghurt |
| 24–27/2/90 | 2096 | ND | Antibiotic breakdown |
| 6–8/3/90 | 125 | $3 \times 10^9$ | After yoghurt. |
| Patient 2 | | | |
| 7–9/3/90 | 1398 | ND | Pretreatment |
| 24–26/4/89 | 0 | $1 \times 10^7$ | After intubation. |
| Patient 3 | | | |
| 19–27/6/89 | 478 | ND | Pretreatment |
| 25–27/9/89 | 208 | $5 \times 10^7$ | After intubation/yoghurts |
| Patient 4 | | | |
| 25–28/11/89 | 309 | ND | Pretreatment |
| 20–22/2/90 | 148 | $2 \times 10^9$ | After yoghurts (never intubated). |
| Patient 5 | | | |
| 10–13/3/90 | 590 | ND | Pretreatment |
| 3–6/4/90 | 329 | $1 \times 10^7$ | After intubation/yoghurts. |
| Patient 6 | | | |
| 15–17/5/90 | 367 | ND | Pretreatment |
| 19–21/6/90 | 128 | $4 \times 10^8$ | After nasopharyngeal tube, then yoghurts |
| Patient 7 | | | |
| 24–27/2/90 | 548 | ND | Pretreatment |
| 13–16/5/90 | 123 | $2 \times 10^7$ | After intubation/yoghurt. |

ND = not detected

TABLE 4

Irritable Bowel Syndrome - patients symptoms index
Determination based on 'Simple index' method of Harvey and Bradshaw (1980). The index is based on the number of stools per day plus other symptoms graded 0 = very well, 1 = slightly below par, 2 = poor, 3 = very poor, 4 = terrible.

| | Pre treatment | Post treatment |
|---|---|---|
| Patient 1 | | |
| Stools per day | 20 | 1 |
| Abdominal pain | 3 | 1 |
| Joint swelling & pain | 2 | 1 |
| | 25 | 3 |
| Patient 2 | | |
| Stools per day | 5 | 1 |
| Headache | 1 | 0 |
| | 6 | 1 |
| Patient 3 | | |
| Stools per day | 4 | 1 |
| Abdominal pain | 2 | 1 |

TABLE 4-continued

Irritable Bowel Syndrome - patients symptoms index
Determination based on 'Simple index' method of Harvey and
Bradshaw (1980). The index is based on the number of stools
per day plus other symptoms graded 0 = very well, 1 = slightly
below par, 2 = poor, 3 = very poor, 4 = terrible.

|  | Pre treatment | Post treatment |
|---|---|---|
| Headache | 2 | 0 |
| Bloating | 1 | 1 |
|  | 9 | 3 |
| Patient 4 | | |
| Not done | | |
| Patient 5 | | |
| Stools per day | 10 | 2 |
| Abdominal pain | 1 | 0 |
| Joint swelling and pain | 2 | 0 |
| Bloating | 3 | 1 |
|  | 16 | 3 |
| Patient 6 | | |
| Stools per day | 4 | 2 |
| Wind | 2 | 1 |
|  | 6 | 3 |
| Patient 7 | | |
| Stools per day | 5 | 1 |
| Abdominal pain | 3 | 1 |
| Bloating | 3 | 1 |
|  | 11 | 3 |
| Patient 8 | | |
| Stools per day | 6 | 7 |
| Abdominal pain | 2 | 2 |
|  | 8 | 9 |
| Patient 9 | | |
| Stools per day | 5 | 3 |
| Abdominal pain | 3 | 2 |
| Bloating | 2 | 3 |
|  | 10 | 8 |
| Patient 10 | | |
| Stools per day | 3 | 1 |
| Headache | 1 | 0 |
| Bloating | 1 | 0 |
|  | 5 | 1 |
| Patient 11 | | |
| Stools per day | 3 | 1 |
| Abdominal pain | 3 | 0 |
| Headache | 3 | 2 |
| Bloating | 3 | 0 |
|  | 12 | 3 |
| Patient 12 | | |
| Stools per day | 8 | 3 |
| Abdominal pain | 2 | 0 |
|  | 10 | 3 |
| Patient 13 | | |
| Stools per day | 3 | 2 |
| Joint swelling and pain | 3 | 1 |
| Headache | 2 | 0 |
|  | 8 | 3 |
| Patient 14 | | |

TABLE 4-continued

Irritable Bowel Syndrome - patients symptoms index
Determination based on 'Simple index' method of Harvey and
Bradshaw (1980). The index is based on the number of stools
per day plus other symptoms graded 0 = very well, 1 = slightly
below par, 2 = poor, 3 = very poor, 4 = terrible.

|  | Pre treatment | Post treatment |
|---|---|---|
| Stools per day | 3 | 1 |
| Abdominal pain | 3 | 0 |
| Headache | 3 | 0 |
| Joint swelling and pain | 2 | 1 |
|  | 11 | 2 |

TABLE 5

| | Symptom index summary | |
|---|---|---|
| Patient | Pre-treatment | Post-treatment |
| 1 | 25 | 3 |
| 2 | 6 | 1 |
| 3 | 9 | 3 |
| 4 | Not done | |
| 5 | 16 | 3 |
| 6 | 6 | 3 |
| 7 | 11 | 3 |
| 8 | 8 | 9 |
| 9 | 10 | 8 |
| 10 | 5 | 1 |
| 11 | 12 | 3 |
| 12 | 10 | 3 |
| 13 | 8 | 3 |
| 14 | 11 | 2 |

EXAMPLE 1

Simultaneous administration to a human patient suffering from IBS, of strain PR88 and a second strain of *Enterococcus faecium*, having apparently identical biochemical and cultural characteristics (identified as PR192), in a single dose, comprising $1\times10^{11}$ PR88 and $1\times10^{11}$ PR192, showed that whereas the faecal excretion of strain PR88 persisted at a level of in excess of $1\times10_5$ per gram wet weight, for over 50 days post-treatment, the excretion of PR192 persisted at a similar level for less than 5 days post-treatment. Furthermore, the patient experienced a reduction in the symptoms of IBS consistent with at least a partial remission, commencing 7 days after treatment and lasting for more than 50 days.

EXAMPLE 2

Daily oral administration to a human patient suffering from IBS, of a dose of $1\times10^{10}$ *Enterococcus faecium* PR88, for a continuous period of 14 days resulted in a daily faecal excretion of the organism in excess of $1\times10^5$ throughout the period of treatment. This was accompanied by an amelioration of the symptoms of IBS, consistent with at least a partial remission of the condition.

EXAMPLE 3

Daily oral administration to a human patient suffering from IBS of a dose of $1\times10^{10}$ of *Enterococcus faecium* PR192, (see Example 1), for a continuous period of 7 days although ensuring a faecal excretion of the organism in excess of $1\times10^5$ per gram wet weight failed to elicit any amelioration of the symptoms of IBS, consistent with remission. The treatment with PR192 was discontinued due to the continued deterioration in the patient's condition. Treatment with PR88 was substituted and resulted in a beneficial response.

EXAMPLE 4

A human patient having a naturally-occurring strain of *Enterococcus faecium*, having identical biochemical and cultural characteristics as PR88 and having a faecal excretion rate of the strain in excess of $1 \times 10^5$ per day, presented with the symptoms of IBS. Administration of a daily oral dose of $1 \times 10^{10}$ of *Enterococcus faecium* PR88 for a period of 14 days resulted in a daily faecal excretion of strain PR88 in excess of $1 \times 10^5$ organisms per gram and an amelioration of the symptoms consistent with at least a partial remission.

These examples indicate that Enterococcus faecium strain PR88 confers a unique benefit in terms of amelioration of the symptoms of IBS consistent with at least a partial remission, not conferred by other strains of *Enterococcus faecium*, whether occurring naturally or administered medicinally.

EXAMPLE 5

*Enterococcus faecium* strain PR88 was maintained in vials frozen in liquid nitrogen. An inoculum for commercial scale production was propagated from frozen vials in a medium consisting of hydrolysed soy protein, yeast extract, glucose, and buffering salts (eg monopotassium hydrogen phosphate and disodium hydrogen phosphate) and a mineral source (eg magnesium sulphate).

For a commercial scale fermentation, a medium consisting of at least one nitrogen source (eg non-fat dry milk, hydrolyzed soy protein, corn steep liquor and yeast extract) is used, with a carbon and energy source (eg glucose or lactose). A mineral source (eg magnesium sulphate) is included to satisfy requirements for kinase reactions. Buffering salts (eg. monopotassium hydrogen phosphate and disodium hydrogen phosphate) are included to prevent acid injury and promote enhanced viable cell recover. The ingredients are uniformly blended in water and sterilized in a pressurized fermenter vessel. The vessel has aseptic attachments for monitoring and controlling temperature and pH. Immediately after exhaustion of the carbon source(s) or just before complete exhaustion, the vessel is cooled to refrigeration temperature, and the cells are harvested by either centriguation or ultrafiltration.

The cold cell concentrate can either be frozen after the addition of cryoprotectants such as sterile milk, lactose or sucrose solution, glycerol, or monosodium glutamate, or frozen as shallow layers in sterile trays and freeze-dried.

In a typical fermentation, a medium consisting of non-fat dry milk at 1%, yeast extract at 1%, lactose or glucose at 2–3%, magnesium sulfate at 0.1%, and a combination of sodium phosphate and potassium phosphate at 0.9% was used. The sterilized medium had an initial pH between 6.3–6.6. Incubation was at 37° C. The pH stat was set at 5.8. After 14–15 hours the cells were harvested by centrifugation to obtain 10×concentration. A cryoprotective mixture of milk and lactose was added to the concentrate before lyophilization. A count of $1.5 \times 10^{11}$ colony forming units per gram of the cell powder was obtained.

EXAMPLE 6

*Enterococcus faecium* strain PR88, prepared as a cell powder in accordance with Example 5, is added by simple admixture to a conventional fermented milk product, eg yoghurt, in an amount sufficient to provide amout $10^9$ viable PR88 organisms per 100 gm of product. Probiotic benefits are derived by a human consuming the product on a regular basis, consistent with normal levels of consumption of such products.

EXAMPLE 7

*Enterococcus faecium* strain PR88 is added to a beverage product in an amount sufficient to provide about $10^9$ viable PR88 organisms per 100 ml of product. The beverage is essentially aqueous, but may contain protein, e.g. cadein or soy, plus minerals and electrolytes.

In general, the probiotic organisms of the invention, especially strain PR88, will be used in medicaments, prophylactics and foodstuffs generally as essentially pure cultures.

REFERENCES

Borody et al, (1980). Medical Journal of Australia, 150, 604. Bowel-flora alteration; a potential cure for inflammatory bowel disease and irritable bowel syndrome.

Burke and Axon (1988). British Medical Journal, 2.97, 102–104. Adhesive *E.coli* in inflammatory bowel disease and infective diarrhoea.

Drossman et al (1982). Gastroenterology, 83, 529–534. Bowel patterns among subjects not seeking health care.

Harvey and Bradshaw (1980). Lancet, March 8. A simple index of Crohn's disease activity.

Hunter and Jones (1985). Irritable Bowel Syndrome edited by N. W. Read. Grune and Stratton. p185–188. Studies on the pathogenesis of irritable bowel syndrome produced by food intolerance.

Jones et al (1982). Lancet, Nov 20, 1115–1117. Food intolerance—a major factor in the pathogenesis of irritable bowel syndrome.

Krag (1985). Scandinavian Journal of Gastroenterology, 109, 107–115. Irritable bowel syndrome; current concepts and future trends.

Manning et al (1978). British Medical Journal, Z, 653–654. Towards a positive diagnosis of the irritable bowel.

Miles and Misra (1938). J. Hygiene, 38, 732–749. The estimation of the bactericidal power of the blood.

Rask-Madsen and Bukhave (1985). Irritable Bowel Syndrome edited by N. W. Reed. Grune and Stratton. p111–122. The irritable bowel syndrome; the role of intestinal secretion.

Thompson and Heaton (1980). Gastroenterology, 79,283–288. Functional bowel disorders in apparently healthy people.

Tilbe and Sullivan (1990). Canadian Medical Association Journal, 142, 539–540. The extracolonic manifestations of the irritable bowel syndrome.

Watson et al (1978). Canadian Medical Association Journal, 118, 387–388. Globus and headache; common symptoms of the irritable bowel syndrome.

We claim:

1. Organisms of *Enterococcus faecium* selected from the group consisting of strain NCIMB 40371 and IBS-alleviating mutants thereof.
2. Organisms of claim 1 in viable form.
3. Organisms of claim 1 in lyophilized form.
4. *Enterococcus faecium* strain NCIMB 40371.

* * * * *